US007803976B2

(12) United States Patent
Clark

(10) Patent No.: US 7,803,976 B2
(45) Date of Patent: Sep. 28, 2010

(54) ALKYLAROMATICS PRODUCTION

(75) Inventor: Michael C. Clark, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/632,230

(22) Filed: Dec. 7, 2009

(65) Prior Publication Data
US 2010/0081853 A1    Apr. 1, 2010

Related U.S. Application Data

(60) Continuation of application No. 12/185,503, filed on Aug. 4, 2008, now Pat. No. 7,652,184, which is a division of application No. 11/343,868, filed on Jan. 31, 2006, now Pat. No. 7,425,659.

(51) Int. Cl.
C07C 2/66 (2006.01)
(52) U.S. Cl. .................................................. 585/467
(58) Field of Classification Search ................. 585/467
See application file for complete search history.

(56) References Cited

U.S. PATENT DOCUMENTS

| 3,766,093 A | 10/1973 | Chu |
| 4,016,218 A | 4/1977 | Haag et al. |
| 4,439,409 A | 3/1984 | Puppe et al. |
| 4,826,667 A | 5/1989 | Zones et al. |
| 4,891,458 A | 1/1990 | Innes et al. |
| 4,954,325 A | 9/1990 | Rubin et al. |
| 4,992,606 A | 2/1991 | Kushnerick et al. |
| 5,077,445 A | 12/1991 | Le |
| 5,081,323 A | 1/1992 | Innes et al. |
| 5,149,894 A | 9/1992 | Holtermann et al. |
| 5,177,285 A | 1/1993 | Van Opdorp et al. |
| 5,191,135 A | 3/1993 | Dwyer et al. |
| 5,198,595 A | 3/1993 | Lee et al. |
| 5,236,575 A | 8/1993 | Bennett et al. |
| 5,250,277 A | 10/1993 | Kresge et al. |
| 5,258,565 A | 11/1993 | Kresge et al. |
| 5,324,877 A | 6/1994 | West et al. |
| 5,362,697 A | 11/1994 | Fung et al. |
| 5,371,310 A | 12/1994 | Bennett et al. |
| 5,453,554 A | 9/1995 | Cheng et al. |
| 5,998,684 A | 12/1999 | Ho et al. |
| 6,077,498 A | 6/2000 | Diaz Cabañas |
| 6,512,153 B1 | 1/2003 | Cappellazzo et al. |
| 6,525,234 B1 | 2/2003 | Dandekar et al. |

FOREIGN PATENT DOCUMENTS

| EP | 0 064 046 | 11/1982 |
| EP | 0 293 032 | 11/1988 |
| EP | 0 432 814 | 6/1991 |
| EP | 0 537 389 | 4/1993 |
| EP | 0 842 914 | 5/1998 |
| EP | 1 069 100 | 1/2001 |
| FR | 2662438 | 11/1991 |
| FR | 2706888 | 12/1994 |
| JP | 07223978 | 8/1995 |
| JP | 11035497 | 2/1999 |
| JP | 11035498 | 2/1999 |
| WO | WO97/17290 | 5/1997 |
| WO | WO01/21562 | 3/2001 |
| WO | WO2005/075387 | 8/2005 |
| WO | WO2005/118476 | 12/2005 |

OTHER PUBLICATIONS

"Atlas of Zeolite Framework Types", eds. Ch. Baerlocher, W. H. Meier, and D. H. Olson, Elsevier, Fifth Edition, 2001.

Primary Examiner—Thuan Dinh Dang
(74) Attorney, Agent, or Firm—Darryl M. Tyus; Xiaobing Feng

(57) ABSTRACT

A process for alkylation of an alkylatable aromatic compound to produce a monoalkylated aromatic compound, comprising the steps of: (a) providing at least one reaction zone having a water content with at least one alkylation catalyst having an activity and a selectivity for said monoalkylated benzene, said alkylation catalyst comprising a porous crystalline molecular sieve of a MCM-22 family material, said MCM-22 family material is characterized by having an X-ray diffraction pattern including d-spacing maxima at 12.4±0.25, 3.57±0.07 and 3.42±0.07 Angstroms; (b) supplying the reaction zone with at least one alkylatable aromatic compound and at least one alkylating agent; (c) operating the reaction zone under suitable alkylation or transalkylation conditions, to produce at least one effluent which comprises a monoalkylated aromatic compound and a polyalkylated aromatic compound(s); (d) monitoring the amount of the monoalkylated aromatic compound or the amount of the polyalkylated aromatic compound(s) in the effluent; (e) adjusting the water content in the reaction zone to secure a desired amount of the monalkylated aromatic compound or the polyalkylated aromatic compound (s) in the effluent, the water content in the reaction zone being in a range from about 1 wppm to about 900 wppm; and wherein the polyalkylated aromatic compound(s) produced is reduced as compared to the reaction zone having a water content of about 0 wppm when the reaction zone is operated under equivalent conditions.

10 Claims, No Drawings

ALKYLAROMATICS PRODUCTION

CROSS-REFERENCE OF RELATED APPLICATIONS

This application is a continuation application of U.S. application Ser. No. 12/185,503, filed Aug. 4, 2008, now U.S. Pat. No. 7,652,184 now allowed, which is a divisional application of U.S. application Ser. No. 11/343,868, filed Jan. 31, 2006, now granted as U.S. Pat. No. 7,425,659 and is fully incorporated herein by reference.

FIELD OF THE INVENTION

The present invention relates to a process for producing alkylated aromatic products, particularly ethylbenzene and cumene.

BACKGROUND OF THE INVENTION

Ethylbenzene is a key raw material in the production of styrene and is produced by the reaction of ethylene and benzene in the presence of an acidic alkylation or transalkylation catalyst. Ethylbenzene production plants built before 1980 used $AlCl_3$ or $BF_3$ as the acidic alkylation or transalkylation catalyst. Plants built after 1980 have in general used zeolite-based acidic catalysts as the alkylation and/or transalkylation catalysts.

Liquid phase ethylation of benzene using a catalyst comprising zeolite beta is disclosed in U.S. Pat. No. 4,891,458 and European Patent Publication Nos. 0432814 and 0629549. More recently it has been disclosed that MCM-22 and its structural analogues have utility in these alkylation/transalkylation reactions, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos. WO97/17290 and WO01/21562 (ITQ-2).

In the prior art alkylation/transalkylation processes, the desired monoalkylated compound is produced along with polyalkylated impurities by contacting an alkylatable aromatic compound and an alkylating agent in the presence of a catalyst. During the alkylation/transalkylation processes, the catalyst ages due to the deposition of coke and other deleterious materials on the catalyst. Such catalyst aging causes a decrease in the catalyst's activity for the conversion of reactants to products. To restore a catalyst's activity, the catalyst is often regenerated by controlled oxidation in air, or by other means. Following regeneration, the catalyst's activity is restored to a certain degree. However, the regenerated catalyst often has a reduced selectivity to produce the desired monoalkylated compound, and increased amounts of the more undesirable polyalkylated impurities are produced. Therefore, there is a need for improved alkylation and/or transalkylation processes that increase and/or control the activity and selectivity of such catalysts to produce the desired monoalkylated aromatic compound in a reaction zone. This invention meets this and other needs.

SUMMARY OF THE INVENTION

In one embodiment, this invention relates to a process for the alkylation or transalkylation of an alkylatable aromatic compound to produce a monoalkylated aromatic compound, comprising the steps of:

(a) providing at least one reaction zone having a water content with at least one catalyst;
(b) supplying the reaction zone with at least one alkylatable aromatic compound and at least one alkylating agent;
(c) operating the reaction zone under suitable alkylation or transalkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent;
(e) adjusting the water content in the reaction zone to secure a desired amount of the monalkylated aromatic compound or the polyalkylated aromatic compound(s) in the effluent, the water content in the reaction zone being in a range from about 1 wppm to about 900 wppm; and wherein the polyalkylated aromatic compound(s) produced is reduced as compared to the reaction zone having a water content of about 0 wppm when the reaction zone is operated under alkylation or transalkylation equivalent conditions.

In another embodiment, this invention relates to a process for alkylation of an alkylatable aromatic compound, to produce a monoalkylated aromatic compound, comprising the steps of:

(a) providing at least one reaction zone having a water content with an amount of at least one catalyst;
(b) supplying the reaction zone with at least one alkylatable aromatic compound and at least one alkylating agent;
(c) operating the reaction zone under suitable alkylation or transalkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent;
(e) adjusting the water content in the reaction zone to secure desired amounts of the monoalkylated aromatic compound and the polyalkylated aromatic compound(s) in the effluent, the water content in the reaction zone being in a range from about 1 wppm to about 900 wppm; and wherein the amount of said catalyst required to produce said desired amounts of monoalkylated aromatic compound and polyalkylated aromatic compound(s) is reduced as compared to said reaction zone having a higher water content than in step (e) and the reaction zone is operated under equivalent alkylation or transalkylation conditions.

In yet another embodiment, this invention relates to a process for alkylation or transalkylation of an alkylatable aromatic compound, to produce a monoalkylated aromatic compound, comprising the steps of:

(a) providing at least one reaction zone having a water content with at least one catalyst, the catalyst having an activity and a selectivity for the monoalkylated aromatic compound;
(b) supplying the reaction zone with at least one alkylatable aromatic compound and at least one alkylating agent;
(c) operating the reaction zone under suitable alkylation or transalkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent; and
(e) controlling the water content in the reaction zone to secure a desired combination of the activity and the selectivity of the catalyst, the water content in the reaction zone being in a range from about 1 wppm to about 900 wppm.

In still yet another embodiment, this invention relates to an apparatus for the production of an monoalkylated aromatic compound, comprising:

(a) a reactor having at least one inlet, at least one reaction zone, and at least one outlet, the inlet adapted to introduce feed stream(s) into the reaction zone, the feed stream(s) comprising at least one an alkylating agent and at least one alkylatable aromatic compound, the reaction zone having a water content and adapted to contain at least one alkylation or transalkylation catalyst, wherein at least one effluent may be produced when the alkylating agent and the alkylatable aromatic compound are contacted in the presence of the alkylation or transalkylation catalyst under suitable alkylation or transalkylation conditions, the effluent which comprises the monoalkylated aromatic compound and polyalkylated aromatic compound(s), the outlet adapted to remove the effluent;

(b) a means for monitoring the amount of the monoalkylated aromatic compound and/or the amount of the polyalkylated aromatic compound(s) in the effluent;

(c) a means for adjusting the water content from about 1 wppm to about 900 wppm in the reaction zone, and whereby a desired combination of the monoalkylated aromatic compound and the polyalkylated aromatic compound(s) may be produced in the reaction zone.

In another embodiment, this invention relates to a method for retrofitting an existing alkylation or transalkylation unit having a reactor as described in step (a) above, comprising the step of adapting said reactor with a means for monitoring the amount of said monoalkylated aromatic compound or the amount of said polyalkylated aromatic compound(s) in said effluent; a means for adjusting said water content from about 1 wppm to about 900 wppm in said reaction zone, and whereby a desired combination of said monoalkylated aromatic compound and said polyalkylated aromatic compound(s) may be produced in said reaction zone.

These and other facets of the present invention shall become apparent from the following detailed description and appended claims.

DETAILED DESCRIPTION OF THE PREFERRED EMBODIMENTS

Feedstocks

The reactants used in the process of the invention include an alkylatable aromatic compound and an alkylating agent. As used herein, an "alkylatable aromatic compound" is a compound that may receive an alkyl group and an "alkylating agent" is a compound which may donate an alkyl group to an alkylatable aromatic compound.

The term "aromatic" as used herein is to be understood in accordance with its art-recognized scope which includes alkyl substituted and unsubstituted mono- and polynuclear compounds. Compounds of an aromatic character, which possess a heteroatom, are also useful provided sufficient activity can be achieved if they act as catalyst poisons under the reaction conditions selected.

Substituted aromatic compounds which may be used for the invention should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this invention include benzene, naphthalene, anthracene, naphthacene, perylene, coronene, and phenanthrene, with benzene being preferred.

Suitable alkyl substituted aromatic compounds that may be used for this invention include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

Suitable alkylating agent(s) that may be used in this invention comprise alkene compound(s) and/or alcohol compound(s), and mixtures thereof. Other suitable alkylating agents that may be useful in the process of this invention generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. It is generally preferred that the alkylating agent has no greater than 5 carbon atoms, more preferably no greater than 3 carbon atoms. Thus the alkylating agent may preferably be selected from the group consisting of $C_2$-$C_5$ olefins and $C_1$-$C_5$ alkanols. The alkylating agent includes a concentrated alkene feedstock (e.g., polymer grade olefins) and a dilute alkene feedstock (e.g., catalytic cracking off-gas).

A concentrated alkene alkylating agent that may be useful in the process of this invention includes an alkene feed comprised of at least 65 mol. % of the alkene and preferably at least 99 mol. % to 100 mol. %.

A dilute alkylating agent that may be useful in the process of this invention includes a dilute alkene feed which contains at least one alkene and a diluent, optionally comprising at least one alkane. For example, where the alkene is ethylene, the alkane may be ethane and/or methane. Preferably, the dilute alkene feed comprises at least 10 mol. % of the alkene, preferably from 20 to 80 mol. % of the alkene. One particularly useful feed is the dilute ethylene stream obtained as an off gas from the fluid catalytic cracking unit of a petroleum refinery.

The term "wppm" as used herein is defined as parts per million by weight. The feed comprising reactants of the present process may contain catalyst poisons.

The term "poison" as used herein means such compounds that are present in trace amounts in the feed(s) comprising the alkylatable aromatic compound(s) or the alkylating agent(s) which may cause deactivation of the alkylation or transalkylation catalyst over time. Catalyst poisons which are strongly sorbed to the alkylation or transalkylation catalyst under alkylation or transalkylation conditions include nitrogen compounds, sulfur compounds, and oxygen compounds of low molecular weight, preferably, no greater than 500, preferably no greater than 300. Such catalyst poison compounds may include ammonia, alkylamines, e.g., methylamine and n-propylamine, N-formyl morpholine and N-methyl pyrrolidine. These catalyst poisons may make up to 100 wppm of the total feed to the process, e.g., 0.001 to 100 wppm.

In one embodiment, the feed(s) comprising the alkylatable aromatic compound(s) and/or alkylating agent(s) may include water. The amount of water in the feed(s) is such that the reaction zone is substantially free of an aqueous phase under the alkylation or transalkylation conditions. The term "substantially free of an aqueous phase", as used herein, means that the reaction zone has less than 5 wt. %, preferably less than 1 wt. %, even more preferably less than 0.5 wt. %, of an aqueous phase under the alkylation or transalkylation conditions. In another embodiment, the amount of water in the feed(s) comprising the alkylatable aromatic compound and/or alkylating agent is such that the reaction zone has less than 900 wppm of water, preferably less than 500 wppm of water, more preferably less than 200 wppm of water, more preferably less than 100 wppm of water, even more preferably less than 50 wppm of water, most preferably less than 10 wppm of water.

In another embodiment, the water content in a reaction zone may be adjusted and/or controlled by the addition of water. In one aspect, a feed comprising liquid water, steam, or a mixture thereof, may be co-fed with the alkylatable aromatic compound and/or alkylating agent to the reaction zone. The amount of water contained in the alkylatable aromatic compound and/or alkylating agent with a co-feed of liquid water and/or steam and/or a mixture thereof is such that the water content in a reaction zone is less than 900 wppm of water, preferably less than 500 wppm of water, more preferably less than 200 wppm of water, more preferably less than 100 wppm of water, even more preferably less than 50 wppm of water, most preferably less than 10 wppm of water. The amount of water contained in the alkylatable aromatic compound and/or alkylating agent together with the co-fed water and/or steam is such that the reaction zone is substantially free of an aqueous phase under the alkylation or transalkylation conditions.

In another embodiment, the water content of the reaction zone is adjusted and/or controlled by removing water from the alkylatable aromatic compound and/or alkylating agent that is fed to the reaction zone. For example, the alkylatable aromatic compound and/or alkylating agent may be dried by a molecular sieve bed before feeding to the reaction zone.

In still yet another embodiment of this invention, the amount of catalyst required to produce a desired amount of monoalkylated aromatic compound and/or polyalkylated aromatic compound(s) is reduced as compared to the amount of catalyst in a reaction zone having a higher water content when the reaction zone(s) are operated under equivalent alkylation or transalkylation conditions.

The amount of catalyst required to produce a desired amount of monoalkylated aromatic compound and/or polyalkylated aromatic compound(s) in a reaction zone having lower water content is reduced by at least 1 wt. %, preferably at least 5 wt. %, more preferably at least 10 wt. %, even more preferably at least 15 wt. %, and most preferably at least about 20 wt. %, as compared to the amount of catalyst required to produce such desired amount of monoalkylated aromatic compound and/or polyalkylated aromatic compound(s) in a reaction zone having 900 wppm water content when the reaction zones are operated under equivalent alkylation or transalkylation conditions, such as, feed composition, temperature, pressure, or weight hourly space velocity ("WHSV"). It is believed that the activity of the catalyst increases when water content in the reaction zone decreases. The term "activity" as used herein refers to the amount of the monoalkylated aromatic compound produced in a reaction zone under certain conditions per unit amount of time per unit volume and may be measured by a reaction rate constant under suitable conditions.

By adjusting and/or controlling the amount of water in a combined feed of the alkylatable aromatic compound and/or alkylating agent to less than 900 wppm of water, preferably less than 500 wppm of water, more preferably less than 200 wppm of water, more preferably less than 100 wppm of water, even more preferably less than 50 wppm of water, most preferably less than 10 wppm of water, the activity of a porous crystalline molecular sieve catalyst or the amount of monoalkylated aromatic compound may be controlled and maintained to a desired range.

In still yet another embodiment of this invention, the amount of the polyalkylated aromatic compound(s) produced in a reaction zone having a water content of above 0 wppm is reduced as compared to the reaction zone having a water content of about 0 wppm when the reaction zone is operated under equivalent alkylation or transalkylation conditions. The selectivity of the catalyst increases when water content in the feed increases. The term "selectivity" as used herein with respect to monoalkylated aromatic compounds refers to the weight ratio of the amount of the monoalkylated aromatic compound produced over the total di-alkylated aromatic compound(s). For example, one measure of the selectivity of the catalyst for cumene may be measured by the weight ratio of the amount of cumene produced over the amount of di-isopropyl benzene produced under total propylene conversion conditions.

In still yet another embodiment of this invention, the selectivity for the monoalkylated aromatic compound is increased as the amount of the polyalkylated aromatic compound(s) produced in a reaction zone having a water content of above 0 wppm is reduced by at least 1%, preferably at least 5%, more preferably at least 10%, even more preferably at least 15%, and most preferably at least 20%, as compared to the reaction zone having a water content of about 0 wppm when the reaction zone is operated under equivalent alkylation or transalkylation conditions.

By adjusting and/or controlling the amount of water in combined feed(s) of the alkylatable aromatic compound and/or alkylating agent to less than 900 wppm of water, preferably less than 500 wppm of water, more preferably less than 200 wppm of water, more preferably less than 100 wppm of water, even more preferably less than 50 wppm of water, most preferably less than 10 wppm of water, the selectivity of a porous crystalline molecular sieve catalyst or the amount of polyalkylated aromatic compound(s) may be controlled and maintained to a desired range.

In still yet another embodiment, this invention relates to a process for alkylation of an alkylatable aromatic compound to produce a monoalkylated aromatic compound, comprising the steps of:

(a) providing at least one reaction zone having a water content with at least one catalyst, the catalyst having an activity and a selectivity for the monoalkylated aromatic compound;
(b) supplying the reaction zone with at least one alkylatable aromatic compound and at least one alkylating agent;
(c) operating the reaction zone under suitable alkylation or transalkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent; and
(e) controlling the water content in the reaction zone to secure a desired combination of the activity and the selectivity of the catalyst, the water content in the reaction zone being in a range from about 1 wppm to about 900 wppm.

Products

Suitable alkyl substituted aromatic compounds which may be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethyl, anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

The feed(s) and effluents of the present process may contain products and catalyst poisons. The poisons in the feed(s) or effluents may be the poisons introduced to the reaction zone in the feed but not sorbed on the catalyst, or the poisons desorbed from the catalyst after contacting with the feed. In one embodiment of this invention, the molar ratio of the poison compound(s) in the effluents over the poison compound(s) in the feed is equal or less than 1.

Poisons in the feed may deactivate catalyst which results in a decrease in the catalyst bed temperature while operating at constant process conditions. Poisons in the feed and/or effluent may be measured by conventional techniques, such as, GC, GC/MS, nitrogen analysis, and sulfur analysis, or other suitable techniques to measure polar compounds and other poisons known to a skilled artisan. The poisons adsorbed on the catalyst may be measured by the difference of the poison compounds on fresh and spent catalyst samples using techniques such as xray flourescence (XRF) and inductively coupled plasma (ICP) that are capable of measuring poison compounds on solid samples or other techniques known to a skilled artisan.

Reaction Conditions

The alkylation reaction is carried out with the alkylatable aromatic compound and the alkylating agent in the reaction zone under conditions to secure at least partially in liquid phase. The alkylation or transalkylation conditions include a temperature of 100 to 285° C. (212 to 545° F.) and a pressure of 689 to 4601 kPa-a (100 to 667 psia), preferably, a pressure of 1500 to 3000 kPa-a (218 to 435 psia), a WHSV based on alkylating agent (e.g., alkene) for overall reactor of 0.1 to 10 $h^{-1}$, preferably, 0.2 to 2 $h^{-1}$, more preferably, 0.5 to 1 $h^{-1}$, or a WHSV based on both alkylating agent and alkylatable aromatics for overall reactor of 10 to 100 $h^{-1}$, preferably, 20 to 50 $h^{-1}$. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a by-passable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

The effluent from the reaction zone comprises the desired alkylated aromatic product, unreacted alkylatable aromatic compound, any unreacted alkylating agent (e.g., alkene, alkene conversion is expected to be at least 90 mol. %, preferably, about 98-99.9999 mol. %) and the alkane component and the other impurities. In one embodiment, at least a portion of the effluent is fed to another reaction zone where an alkylating agent is added for reaction with the unreacted alkylatable aromatic compound with an alkylation or transalkylation catalyst. Furthermore, at least a portion the effluent from any of the reaction zone(s) may be fed directly or indirectly to a transalkylation unit.

The term "at least partially in liquid phase" as used herein is understood as a mixture having at least 1 wt. % liquid phase, optionally at least 5 wt. % liquid phase at a given temperature, pressure, and composition.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the alkene. However, for some applications, it may be desirable to operate at below 100% alkene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by a transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a (100 to 667 psia), preferably, a pressure of 1500 to 4137 kPa-a (218 to 600 psia), a WHSV based on total ethylene and total catalyst for overall reactor of 0.1 to 10 $h^{-1}$, preferably, 0.2 to 2 $h^{-1}$, more preferably, 0.5 to 1 $h^{-1}$, or a WHSV based on both total ethylene and benzene, and total catalyst for overall reactor of 10 to 100 $h^{-1}$, preferably, 20 to 50 $h^{-1}$, and a molar ratio of benzene to ethylene from about 1 to about 10.

Particular conditions for carrying out the at least partially in liquid phase alkylation of benzene with propylene may include a temperature of from about 80 to 160° C., a pressure of about 680 to about 4800 kPa-a; preferably from about 100 to 140° C. and pressure of about 2000 to 3000 kPa-a, a WHSV based on propylene of from about 0.1 about 10 $hr^{-1}$, and a molar ratio of benzene to ethylene from about 1 to about 10.

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kPa-a (100 to 667 psia), preferably, a pressure of 1500 to 4137 kPa-a (218 to 600 psia), a WHSV based on total ethylene and the total amount of catalyst for the overall reactor of 0.1 to 10 $h^{-1}$, preferably, 0.2 to 2 $h^{-1}$, more preferably, 0.5 to 1 $h^{-1}$, or a WHSV based on both total ethylene and total benzene, and the total amount of catalyst for the overall reactor of 10 to 100 $h^{-1}$, preferably, 20 to 50 $h^{-1}$, and a molar ratio of benzene to ethylene from about 1 to about 10.

The transalkylation reaction may take place under at least partially in liquid phase conditions. Particular conditions for carrying out the at least partially in liquid phase transalkylation of polyalkylated aromatic compound(s), e.g., polyethylbenzene(s) or polyisopropylbenzene(s), with benzene may include a temperature of from about 100° to about 300° C., a pressure of 696 to 4137 kPa-a (101 to 600 psia), a WHSV based on the weight of the polyalkylated aromatic compound (s) feed to the alkylation reaction zone of from about 0.5 to about 100 $hr^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), e.g., polyethylbenzene(s) or polyisopropylbenzene(s), with benzene may include a temperature of from about 350 to about 450° C., a pressure of 696 to 1601 kPa-a (101 to 232 psia), a WHSV based on the weight of the polyalkylated aromatic compound(s) feed to the reaction zone of from about 0.5 to about 20 $hr^{-1}$, preferably, from about 1 to about 10 $hr^{-1}$, and a molar ratio of benzene to polyalkylated aromatic compound(s) of from 1:1 to 5:1, preferably, 2:1 to 3:1.

Catalysts

In one embodiment of this invention, the alkylation or transalkylation catalyst that may be used in this invention is a porous crystalline molecular sieve having a zeolite framework type of at least one of MWW, FAU, *BEA, or any combination thereof. In another embodiment, the porous crystalline material comprises at least one of zeolite beta, zeolite Y, Ultrastable Y (USY), Dealuminized Y (Deal Y), mordenite, ERB-1, ITQ-1, ITQ-2, ITQ-30, rare earth exchanged Y (REY), PSH-3, SSZ-25, MCM-22, MCM-36, MCM-49, MCM-56, or a MCM-22 family material. In one embodiment, the catalyst of this invention may or may not have metal function, such as hydrogenation function provided by noble metal(s), e.g., metal(s) of Groups III, IV, V, VI, VII, and VIII of periodic table. In yet another embodiment, the catalyst of this invention may or may not have a zeolite having a zeolitic framework type of MFI, e.g., silicalite or ZSM-5.

The term "MCM-22 family material", as used herein, includes (a) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth Edition, 2001, the entire contents of which is incorporated as reference;

(b) molecular sieves made from a common second degree building block, a 2-dimensional tiling of such MWW framework type unit cells, forming a "monolayer of one unit cell thickness", preferably one c-unit cell thickness;

(c) molecular sieves made from common second degree building blocks, "layers of one or more than one unit cell thickness", wherein the layer of more than one unit cell thickness is made from stacking, packing, or binding at least two monolayers of one unit cell thick. The stacking of such second degree building blocks can be in a regular fashion, an irregular fashion, a random fashion, or any combination thereof; and (d) molecular sieves made by any 1-dimensional, 2-dimensional or 3-dimensional combination of unit cells having the MWW framework topology.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this invention have minor proportion (less than 50 wt. %), preferably less than 20 wt. %, more preferably less than 10 wt. %, even more preferably less than 5 wt. %, and most preferably less than 1 wt. %, of such impurities in the MCM-22 family materials, which weight percent (wt. %) values are based on the combined weight of impurities and pure phase MCM-22 family materials.

In one embodiment, the MCM-22 family materials are characterized by having an X-ray diffraction pattern including d-spacing maxima at 12.4±0.25, 3.57±0.07 and 3.42±0.07 Angstroms (either calcined or as-synthesized). In another embodiment, the MCM-22 family materials are characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U. S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077, 498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore zeolite alkylation or transalkylation catalysts, such as mordenite, in that catalysis in MCM-22 materials occurs in 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25. The zeolites of the MWW type are described as having varied uses. U.S. Pat. No. 4,826,667 describes zeolite SSZ-25 as useful primarily for catalyzed hydrocarbon conversion reactions, such as catalytic cracking, hydrocracking, hydrodewaxing, olefin and aromatics formation reactions such as xylene isomerization, but also as an adsorbent, as a filter and as a water-softening agent. U.S. Pat. No. 4,954,325 lists 16 different uses for the material now known as MCM-22.

Alternatively, the alkylation and/or transalkylation catalyst may further comprise a medium pore molecular sieve having a Constraint Index of 2-12 (as defined in U.S. Pat. No. 4,016, 218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In another embodiment, the alkylation and/or transalkylation catalyst may comprise a large pore molecular sieve having a Constraint Index of less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

Molecular sieves and/or zeolites that may find application in the present invention include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. Ch. Baerlocher, W. H. Meier, and D. H. Olson, Elsevier, Fifth Edition, 2001, which is hereby incorporated by reference. A summary of the prior art, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

The stability of the catalyst(s) used in the present process may be increased by steaming. U.S. Pat. Nos. 4,663,492; 4,594,146; 4,522,929; and 4,429,176, describe conditions for the steam stabilization of zeolite catalysts which may be utilized to steam-stabilize the catalyst. Reference is made to these patents for a detailed description of the steam stabilization technique for use with the present catalysts. The steam stabilization conditions typically include contacting the catalyst with, e.g., 5-100% steam at a temperature of at least about 300° C. (e.g., 300°-650° C.) for at least one hour (e.g., 1-200 hours) at a pressure of 101-2,500 kPa-a. In a more particular embodiment, the catalyst may be made to undergo steaming with 75-100% steam at 315°-500° C. and atmospheric pressure for 2-25 hours. The steaming of the catalyst may take place under conditions sufficient to initially increase the Alpha Value of the catalyst, the significance of which is discussed below, and produce a steamed catalyst having an enhanced Alpha Value. If desired, steaming may be continued to subsequently reduce the Alpha Value from the higher Alpha Value to an Alpha Value which is substantially the same as the Alpha Value of the unsteamed catalyst.

The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Apparatus

In one embodiment, this invention relates to an apparatus for the production of a monoalkylated aromatic compound, comprising:

(a) a reactor having at least one inlet, at least one reaction zone, and at least one outlet, the inlet adapted to introduce feed stream(s) into the reaction zone, the feed stream(s) comprising at least one an alkylating agent and at least one alkylatable aromatic compound, the reaction zone having a water content and adapted to contain at least one alkylation or transalkylation catalyst, wherein at least one effluent may be produced when the alkylating agent and the alkylatable aromatic compound are contacted in the presence of the alkylation or transalkylation catalyst under suitable alkylation or transalkylation conditions, the effluent which comprises the monoalkylated aromatic compound and polyalkylated aromatic compound(s), the outlet adapted to remove the effluent;

(b) a means for monitoring the amount of the monoalkylated aromatic compound or the amount of the polyalkylated aromatic compound(s) in the effluent;

(c) a means for adjusting the water content from about 1 wppm to about 900 wppm in the reaction zone, and whereby a desired combination of the monoalkylated aromatic compound and the polyalkylated aromatic compound(s) may be produced in the reaction zone.

In one aspect of this invention, the means for adjusting the water content of the reaction zone includes introducing water to the reaction zone in the form of steam, liquid water, or a mixture thereof. Other such means include removing water from the alkylatable aromatic compound and/or the alkylating agent by drying with a molecular sieve or dehydration by distillation, or other suitable means known to those skilled in the art or by combinations of these techniques such as distillation followed by drying over a molecular sieve or clay.

It is well know to a person skilled in the art that the means for monitoring the amount of the monoalkylated aromatic compound or the amount of the polyalkylated aromatic compound include any conventional techniques, such as, online or offline Gas Chromatograph (GC), online or offline Gas Chromatograph Mass Spectrometer (GC-MS), material balance analysis, FTIR, UV, elementary analysis, density analysis, gravity analysis, other suitable techniques to measure aromatic compound known to a skilled artisan, and any combination thereof.

In an alternative embodiment of this invention includes a method for retrofitting an existing alkylation unit having a reactor as described above. This method comprises the step of adapting said reactor with a means for monitoring the amount of said monoalkylated aromatic compound or the amount of said polyalkylated aromatic compound(s) in said effluent; a means for adjusting said water content from about 1 wppm to about 900 wppm in said reaction zone, and whereby a desired combination of said monoalkylated aromatic compound and said polyalkylated aromatic compound(s) may be produced in said reaction zone. This method is suitable for retrofitting an existing ethylbenzene or cumene plant with a vapor phase, at least partial liquid phase, or mixed phase alkylation reactor. In particular, the process of this invention may be used to retrofit an existing ethylbenzene or cumene plant using polymer grade or chemical grade ethylene or propylene with minimum amount of new equipment, such as, extra compressors for the alkylating agent, extra-separation column for light gas and aromatics, and other equipment.

The invention will be more particularly described with reference to the following Examples.

Testing Procedures

Feed Pretreatment

Benzene (99.96 wt. %) was obtained from the ExxonMobil Baytown Chemical plant. The benzene was passed through a pretreatment vessel (2L Hoke vessel) containing absorbent materials from inlet to outlet. All absorbent feed pretreatment materials were dried in a 260° C. oven for 12 hours before using.

Polymer grade propylene was obtained from Scott Specialty Gases (Pasadena, Tex., USA). Propylene was passed through a 300 ml vessel containing absorbents which were dried in a 260° C. oven for 12 hours before using.

Ultra high purity grade Nitrogen was obtained from Scott Specialty Gases. Nitrogen was passed through a 300 ml vessel containing absorbents which were dried at 260° C. for 12 hours before using.

Catalyst Preparation and Loading

MCM-22 catalyst was prepared according to U.S. Pat. No. 4,954,325, the whole content of which is incorporated herein as reference. MCM-49 catalyst was prepared according to U.S. Pat. No. 5,236,575, the whole content of which is incorporated herein as reference.

Catalyst activity was calculated using the second order rate constant under the reaction conditions (temperature 130° C. and pressure 2170 kPa-a). Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of cumene produced over di-isopropyl benzenes under the reaction conditions (temperature 130° C. and pressure 2170 kPa-a).

Two grams of catalyst was dried in air at 260° C. for 2 hours. The catalyst was removed immediately after drying. The bottom of a catalyst basket was packed with quartz chips followed by loading of one gram of catalyst into basket on top of the quartz chips. The catalyst was then covered by additional quartz chips. The catalyst basket containing the catalyst and quartz chips was dried at 260° C. in air for about 16 hours.

Before each experiment the reactor and all lines were cleaned with a suitable solvent (such as toluene) followed by flowing of air after cleaning to remove all cleaning solvent. The catalyst basket containing the catalyst and quartz chips was placed in reactor immediately after drying.

A 300 ml Parr® batch reaction vessel (Series 4563 mini Bench top reactor with a static catalyst basket, Parr Instrument Company, Moline, Ill. USA) equipped with a stir rod and static catalyst basket was used for the activity and selectivity measurements. The reaction vessel was fitted with two removable vessels for the introduction of benzene and propylene respectively.

The reactor was purged with 100 ml/min of the treated ultra high purity nitrogen, $N_2$, for 2 hours at 170° C. Then, the reactor temperature was reduced to 130° C. under nitrogen flow. All inlets and outlets of the reactor were closed off afterward. Pretreated benzene (156.1 gram) was transferred into the reactor under 791 kPa-a ultra high purity nitrogen blanket. The reactor was stirred at 500 rpm for 1 hour. Pretreated liquid propylene (28.1 gram) under 2170 kPa-a ultra high purity nitrogen is then transferred to the reactor. The reactor was maintained at 2170 kPa-a by the 2170 kPa-a ultra high purity nitrogen. Liquid samples were taken at 30, 60, 120, 150, 180 and 240 min after addition of the propylene.

Water was added to the reaction mixture by either of two methods. First, the water was added to the pretreated benzene supply to obtain the desired water level in the reaction mixture. Second, the pre-dried catalyst was humidified until the proper amount of water adsorbed corresponding to the desired amount of water in the reaction mixture was obtained. The amount of water in the reaction product at end of test was measured by Karl Fischer Titrator (Mettler Toledo, Inc., Columbus, Ohio, USA) which is typically accurate to within 50 wppm.

EXAMPLES

One gram MCM-22 catalyst (65 wt. % MCM-22 and 35 wt. % alumina), one gram MCM-49 catalyst (80 wt. % MCM-22 and 20 wt. % alumina), and one gram zeolite beta catalyst (80 wt. % Beta, $Si/Al_2$ of 24, and 20 wt. % alumina) were tested under the conditions and method described above.

The activity of the zeolite beta catalyst increased by 88% at 0 wppm $H_2O$ as comparing to the activity of the zeolite beta catalyst at same conditions except at a water content of 872 wppm. The activity of the zeolite MCM-22 catalyst increased by 544% at 0 wppm $H_2O$ and 22% at 448 wppm $H_2O$ as comparing to the activity of the zeolite MCM-22 catalyst at same conditions except water content of 922 wppm. The activity of the zeolite MCM-49 catalyst increased by 497% at 0 wppm $H_2O$ and 39% at 474 wppm $H_2O$ as compared to the activity of the zeolite MCM-49 catalyst at same conditions except water content of 885 wppm.

The selectivity of the zeolite beta catalyst increased from 4.76 at 0 wppm $H_2O$ to 14.49 at 872 wppm $H_2O$ as compared to the selectivity of the zeolite beta catalyst at the same conditions except at a water content of 0 wppm. The selectivity of the zeolite MCM-22 catalyst increased by 44% at 922 wppm $H_2O$ and 41% at 211 wppm $H_2O$ as compared to the selectivity of the zeolite MCM-22 catalyst at same conditions except water content of 0 wppm. The selectivity of the zeolite MCM-49 catalyst increased by 78% at 885 wppm $H_2O$ and 36% at 474 wppm $H_2O$ as compared to the selectivity of the zeolite MCM-49 catalyst at same conditions except at a water content of 0 wppm.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for alkylation of benzene with at least one alkylating agent to produce a monoalkylated benzene, comprising the steps of:
    (a) providing at least one reaction zone having a water content with at least one alkylation catalyst having an activity and a selectivity for said monoalkylated benzene, said alkylation catalyst comprising a porous crystalline molecular sieve having a framework type MWW combined with either FAU or *BEA;
    (b) supplying said reaction zone with said benzene and said at least one alkylating agent;
    (c) operating said reaction zone under suitable alkylation conditions, to produce at least one effluent which comprises a monoalkylated benzene and polyalkylated benzene(s);
    (d) monitoring said amount of said monoalkylated benzene or said amount of said polyalkylated benzene(s) in said effluent; and
    (e) adjusting said water content in a range from about 1 wppm to about 900 wppm in said reaction zone to secure a desired combination of said activity and said selectivity of said alkylation catalyst based on said amount of said monoalkylated benzene or said polyalkylated benzene(s) of (d).

2. The process of claim 1, wherein said at least one alkylating agent is selected from the group consisting of ethylene, propylene, butenes and pentenes.

3. The process of claim 1, wherein said at least one alkylating agent is selected from the group consisting of methanol, ethanol, propanols, butanols and pentanols.

4. The process of claim 1, wherein said monoalkylated benzene comprises ethylbenzene and said alkylating agent comprises ethylene or ethanol.

5. The process of claim 1, wherein said monoalkylated benzene comprises cumene and said alkylating agent comprises propylene or propanols.

6. The process of claim 1, wherein said monoalkylated benzene comprises sec-butyl-benzene and said alkylating agent comprises butylene or butanols.

7. The process of claim 1, wherein said water content of said reaction zone is selected from the group consisting of less than about 500 wppm, less than about 200 wppm, less than about 100 wppm and less than about 50 wppm.

8. The process of claim 1, further comprising a finishing reactor downstream of said reaction zone.

9. The process of claim 1, wherein said suitable alkylation conditions include a temperature from about 100° C. to about 400° C., a pressure from about 20.3 to 4500 kPa-a, a WHSV from about 0.1 to about 10 $h^{-1}$, and a molar ratio of said over said alkylating agent from about 0.1:1 to 50:1.

10. The process of claim 6, wherein said suitable alkylation conditions maintain said reaction zone in at least partial liquid phase conditions.

* * * * *